United States Patent [19]

Widder et al.

[11] Patent Number: 4,844,882

[45] Date of Patent: Jul. 4, 1989

[54] CONCENTRATED STABILIZED MICROBUBBLE-TYPE ULTRASONIC IMAGING AGENT

[75] Inventors: Kenneth J. Widder, Del Mar; Peter J. Westkaemper, San Diego, both of Calif.

[73] Assignee: Molecular Biosystems, Inc., San Diego, Calif.

[21] Appl. No.: 139,576

[22] Filed: Dec. 29, 1987

[51] Int. Cl.$^4$ .............................................. A61K 49/00
[52] U.S. Cl. ...................................... 424/9; 514/945; 128/660.01
[58] Field of Search ............................ 424/9; 514/945; 128/660–663

[56] References Cited

U.S. PATENT DOCUMENTS

| | | | |
|---|---|---|---|
| 4,276,885 | 7/1981 | Tickner et al. | 128/660 |
| 4,466,442 | 8/1984 | Hilmann et al. | 128/653 |
| 4,572,203 | 2/1986 | Feinstein | 128/661 |
| 4,718,433 | 1/1988 | Feinstein | 128/660 |
| 4,774,958 | 10/1988 | Feinstein | 128/660.01 |

OTHER PUBLICATIONS

Tickner et al., National Technical Information Service Report HR 62917-1A, Apr. 1977, pp. 34–40.
Feinstein et al., (1984), J. Am. Coll. Cardio., 3:14–20.
Keller et al., (1987), Amer. Heart J., 114:570–575.

*Primary Examiner*—Douglas W. Robinson
*Assistant Examiner*—Raymond J. Henley, III
*Attorney, Agent, or Firm*—Tilton, Fallon, Lungmus & Chestnut

[57] ABSTRACT

A microbubble-type ultrasonic imaging agent is provided comprising a parenterally-administerable aqueous medium containing a dispersion of microspheres predominantly of diameters less than 10 microns, wherein the microspheres consist of gas microbubbles encapsulated with water-insolubilized biocompatible material. The imaging agent is characterized by having a concentration of greater than $100 \times 10^6$ microspheres per milliliter, and a stability such that this concentration is maintained for over 4 weeks at a temperature of 20° to 25° C.

8 Claims, 4 Drawing Sheets

CONCENTRATED STABILIZED MICROBUBBLE-TYPE ULTRASONIC IMAGING AGENT

FIELD OF INVENTION

This invention relates to ultrasonic imaging of the human body for diagnostic purposes; and, more particularly, to ultrasonic imaging agents.

BACKGROUND OF INVENTION

It has been known since 1968–70 that contrast echocardiography can be used to delineate intracardiac structures, assess valvular competence, demonstrate intracardiac shunts, and identify pericardial effusion. (Gramiak and Shah, 1968; and Feigenbaum, et al., 1970.) Ultrasonic imaging of the heart potentially has important advantages of convenience, safety, and reduced cost over present diagnostic procedures, such as angiography, which requires the use of radio-opaque dyes for X-ray imaging, or the use of radio-nuclide imaging agents for radio-imaging. However, progress in practical applications of ultrasonic imaging has been delayed by the lack of effective clinically-usable imaging agents.

Ultrasonic imaging utilizes an ultrasonic scanner to generate and receive sound waves. The scanner is placed on a body surface overlying the area to be imaged, and sound waves are directed toward that area. The scanner detects reflected sound waves and translates that data into images. When ultrasonic energy is transmitted through a substance, the acoustic properties of the substance depend upon the velocity of the transmission and the density of the substance. Changes in the substance's acoustic properties (e.g., variations in acoustic impedance) are most prominent at the interfaces of different substances, such as a liquid-solid or liquid-gas interface. Consequently, when ultrasonic energy is directed through media, changes in acoustic properties will result in more intense sound reflection signals for detection by the ultrasonic scanner.

Ultrasonic imaging agents can consist of small solid or gaseous particles which, when injected in the circulatory system, provide improved sound reflection and image clarity. Microbubble-type imaging agents consist of minute bubbles of a gas (usually air) which are dispersed in a carrier liquid for parenteral injection. The "microbubbles" are carried by the circulatory system to the organ being imaged.

It has been proposed to form a dispersion of air microbubbles in a warm aqueous gelatin solution, and cooling the solution to a solidification temperature to trap the microbubbles. For administration, the gelled dispersion is to be warmed until it liquifies, and parenterally administered with the microbubbles dispersed in the liquified gelatin. (Tickner, et al. U.S. Pat. No. 4,276,885;- and Tickner, et al., National Technical Information Service Report HR62917-1A, April, 1977).

Gelatin-trapped microbubbles on introduction into the bloodstream have a short life-time. They rapidly dissipate. Another disadvantage is that the microbubbles are too large to pass through capillary beds, and are therefore not suitable for heart imaging by peripheral intravenous administration.

The discovery by Dr. Steven B. Feinstein of sonication-produced microbubble imaging agents represented an important advance in this art. Using viscous aqueous solutions, such as 70% sorbitol or dextrose, Dr. Feinstein produced a dispersion of microbubbles by high energy sonication of the solutions. The resulting microbubbles had sizes less than 10 microns, and were capable of passing through capillary beds. The persistence of the microbubbles, although of the order of a few minutes, permitted the imaging agent to be pre pared and administered intravenously for heart imaging. (Feinstein, et al., 1984; and Feinstein U.S. Pat. No. 4,572,203.)

Subsequently, Dr. Feinstein sought to improve the persistence of the microbubbles. He found that by sonication of a heat-sensitive protein, such as albumin, microbubbles of improved stability were obtained. (See Feinstein, PCT Application WO No. 84/02838, corresponding to allowed U.S. application Ser. No. 805,975, filed Dec. 5, 1985, now U.S. Pat. No. 4,718,433). Concentrations of microbubbles of 10 to $14 \times 10^6$ microbubbles per milliliter were obtained with bubble sizes from 2 to 9 microns (Keller, Feinstein, and Watson, 1987). The microbubbles persisted for 24 to 48 hours.

However, the sonication-produced albumin microbubble imaging agent of Feinstein was not sufficiently stable for commercial manufacture. Stabilities of the order of weeks or months (rather than hours or days) are required to permit an imaging agent to be manufactured at a central location and distributed to hospitals in the United States and other countries. For commercially feasible manufacture, shipment and hospital storage prior to use, a stability time of at least four weeks is needed and preferably at least eight weeks or longer.

Further, for the most effective imaging, it is desirable to have the highest obtainable concentration of microbubbles in the imaging agent. But the population of microbubbles of the desired small sizes tends to decrease with holding of the sonicated albumin solutions. The small bubble size attrition can occur either by collapse of the microbubbles, or by coalesence to oversize microbubbles. Consequently a further important objective has been to find means for increasing concentrations of microbubbles in the imaging agent. An imaging agent of very high microbubble concentration is inherently better, and a safety factor is provided. With a concentration of microbubbles higher than the minimum required for effective imaging, some loss of the microbubbles of the desired size can be accepted.

SUMMARY OF INVENTION

The present invention provides an ultra-concentrated, room-temperature stable microbubble-type imaging agent. This improved imaging agent comprises a sterile aqueous medium containing a dispersion of microspheres predominantly of diameters less than 10 microns, and is thereby suitable for parenteral intravenous administration. The microspheres consist of gas microbubbles encapsulated in a water-insolubilized biocompatible material, such as albumin. Representing a substantial advance in the art, the imaging agent of this invention has a homogeneously dispersed concentration of greater than $100 \times 10^6$ (e.g., $10^8$) microspheres per milliliter. This high concentration can be maintained at ordinary room temperatures (20° to 25° C.) for extended periods of time (4 to 8 weeks or longer). In optimized embodiments, microsphere concentrations of the order of 300 to $500 \times 10^6$ microspheres per milliliter are achieved. Surprisingly, these ultra-high concentrations can be maintained for over eight weeks. The imaging agents of this invention are therefore adapted for manufacture and distribution on a commercial basis. Following shipment, they may be maintained in inventory by hospitals for many weeks, being available for diagnostic use as required.

The imaging agents of this invention are preferably produced from a heat-denaturable biocompatible protein by a stepwise sonication procedure. As with the Feinstein method, an aqueous solution of protein is subjected to sonication to form gas microbubbles while concurrently heating the solution to insolubilize small portions of the protein. However, the improved sonication procedure, which results in the increased concentration of highly stable microbubbles utilizes a novel sequential sonication. In the initial sonication phase, the sonicator horn is directly contacted with the solution (viz. by immersion just below the upper surface of the solution). This initial sonication is carried out without appreciable foaming of the solution. In the next phase of the sonication, foaming is promoted. The sonicator horn is withdrawn to a position in the ambient atmosphere above but proximate to the surface of the solution. Intense foaming and aerosolating occurs. The population of microbubbles is thereby greatly increased and the microbubbles are encapsulated with denatured protein to obtain a dispersion of highly stable microspheres. Moreover, the stability of the microspheres permits them to be concentrated and/or fractionated. By such manipulations, bubble concentration can be doubled or tripled and oversize bubbles eliminated.

For example, the concentration of the microspheres as initially produced can be from 50 to $150 \times 10^6$ By a float separation concentration procedure, the microsphere concentration can be increased 200 to $600 \times 10^6$ microspheres per milliliter. Also, by another float-type separation, most of the microbubbles of larger size than 10 microns can be removed, resulting in an imaging agent composed predominantly of microspheres of diameters substantially less than 10 microns. For example, at least 80% of the microspheres can have diameters in the range from 1 to 9 microns.

THE DRAWINGS

The accompanying drawings illustrate a preferred method of preparing the ultrasound imaging agent of this invention.

Figure 4:
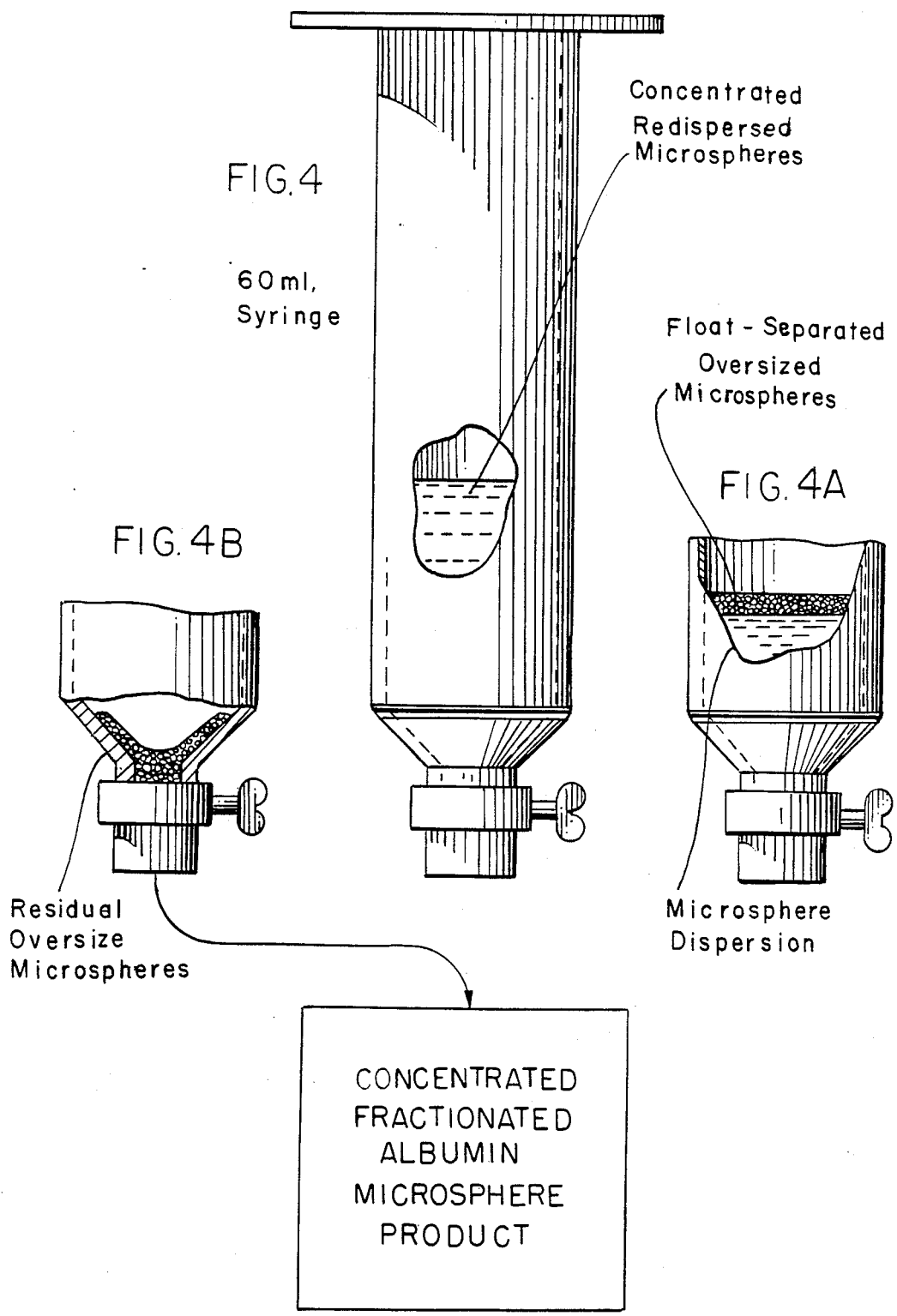

FIGS. 4, 4A, and 4B illustrate a method of fractionation of microsphere dispersions to remove oversize microspheres.

Figure 5:
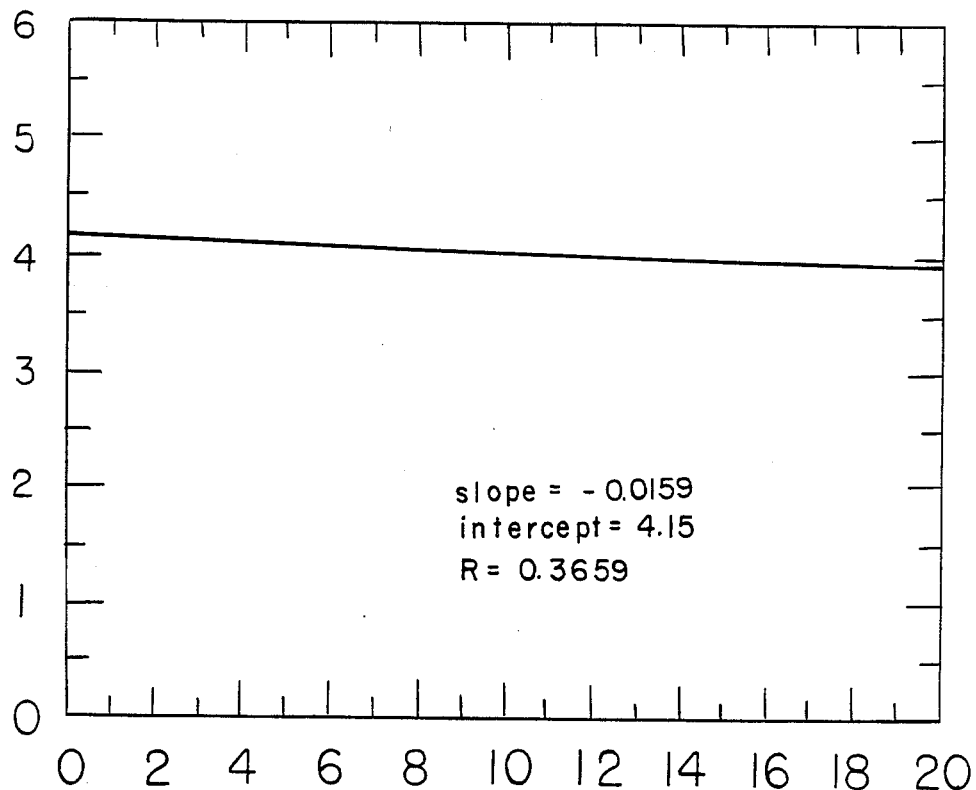

FIG. 5 is a graph of experimental data showing the concentration of the microspheres in the imaging agent as produced, and their storage stability.

DETAILED DESCRIPTION

The starting material for practicing this invention is an aqueous solution of a suitable biocompatible material. The encapsulating material should be heat-sensitive so that it can be partially insolubilized by heating during sonication. More specifically, coincident with the sonication, a small portion of the dissolved biocompatible material is heated or otherwise treated so that its solubility is reduced. This results in a small volume of solid phase material, which forms the encapsulating layers around the microspheres. Preferably a heat-sensitive protein is selected such as albumin, hemoglobin, collagen, etc. For administration to humans, human protein is preferred. Human serum albumin (HSA) is especially suitable. HSA is available commercially as a sterile 5% aqueous solution, which can be used directly as the starting material for preparing the microspheres. However, other concentrations of albumin or other heat-denaturable proteins can be used. HSA concentration can be varied, for example, within the range from 1 to 25% by weight.

Commercially-available sonicator equipment may be used in practicing this invention. Theoretically, sonicator vibration frequencies can vary over a considerable range, such as from 5 to 30 kiloHerz (kHz), but most commercially-available sonicators operate at 20 kHz or 10 kHz. The 20 kHz sonicators perform well for purpose of this invention. Such sonicator equipment can be obtained from Heat Systems-Ultrasonics, Inc., Farmingdale, N.Y., and other companies. Ultrasonics Model W-380 or similar model can be used with a flat tip, high gain sonicator horn. The power applied to the sonicator horn can be varied over power settings scaled from 1 to 10 by the manufacturer, as with Ultrasonics Model W-380. An intermediate power setting can be used (viz. from 4 to 8). The vibrational frequency and the power applied must be sufficient to produce cavitation in the liquid being sonicated.

The solution to be sonicated can be treated in small increments. For example, 8 ml. quantities of the solution can be individually sonicated. Initial sonication can be carried out with the flat-ended sonicator horn in contact with the solution, preferably immersed in the upper portion of the solution. Immersion is desirable in order to carry out the initial sonication without appreciable foaming. With a power setting of 4 to 6, the initial sonication can be performed in less than a minute (viz. 15 to 45 seconds).

Immediately following the initial phase of the sonication, the sonicator horn is withdrawn to a position above the solution but proximate to the upper surface of the solution. In the second phase, the sonication is deliberately carried out in such manner as to produce intense foaming of the solution, contrary to conventional sonications, where it is desirable to avoid foaming. For the purpose of the present invention, foaming and aerosolating are important for obtaining the imaging agent of enhanced concentration and stability.

To promote foaming, the power input to the sonicator horn may be increased in the second stage. For example, the power setting may be moved from an initial setting of 4 to a setting of 6. The second phase of the sonication can be carried out in less than a minute, (viz. from 15 to 45 seconds). The total time for the sonication for both the first and second phases can be of the order of one minute. For example, a 25 to 35 second sonication can be used for each phase. The foaming produced in the second phase of the sonication is immediately detectable by the cloudy appearance of the solution, and by the foam produced.

By means of the sequential sonication, comprising the cavitation phase followed by a foaming phase, the concentration of the encapsulated microbubbles, referred to herein as "microspheres", can be greatly increased. Concentrations in excess of $25 \times 10_6$ microspheres per milliliter are easily obtainable, such as from 50 to $150 \times 10^6$ concentrations. Moreover, the resulting microspheres will be predominantly of diameters less than 10 microns. For example, 80% or more of the microspheres can have diameters in the range from 1 to 9 microns with a mean diameter of 4 to 6 microns.

When the sonication is carried out in contact with air as the ambient atmosphere, the microspheres will have air centers. Air is believed to be the most convenient ambient atmosphere, but, if desired, sonication could be carried out under other gas atmospheres (viz. nitrogen, oxygen, carbon dioxide, etc.).

Following initial production, the microsphere dispersions can be further processed to increase the concentration and/or to remove oversize microspheres. Since the microspheres are buoyant they tend to rise to the surface of the dispersion. By holding the dispersion without agitation for a number of hours, (viz. for 4 to 12 hours), most of the microspheres will rise to the surface and concentrate in an upper layer above the clarified solution. By this "float-separation" of the microspheres into an upper layer, portions of the clarified solution can be removed from below the microspheres, thereby obtaining a dispersion of greater microsphere concentration. For example, from 50 to 75% of the solution volume may be removed in this concentration process.

Either before or after the above-described concentration, float-separation of oversized microspheres can be obtained. Large size microspheres such as one having diameters greater than 10 microns have relatively greater buoyancy. They will therefore rise more rapidly to the surface of the solution. By utilizing a short holding time, such as from 15 to 45 minutes, the largest size microspheres can be selectively collected in a small upper layer above a dispersion which will still contain substantially all of the microspheres of small size. By removing this microsphere dispersion from beneath the layer of oversize microspheres, a fractionation may be achieved in which the larger microspheres will remain in the vessel in which the fractionation is carried out.

The imaging agent produced by this combination of two-stage sonication and the float-separation concentration can have a homogeneously-dispersed concentration of greater than $300 \times 10^6$, such as from 300 to $900 \times 10^6$ ($3 \times 10^8$ to $9 \times 10^8$) microspheres per milliliter. High concentrations can be maintained for long periods of holding at ambient room temperatures (20°–25° C.). Concentrations above 200 and typically above $300 \times 10^6$ microspheres per milliliter can be maintained for periods of at least four and usually eight weeks or longer.

ILLUSTRATIVE EMBODIMENTS

Figures 1A, 1B, 1C:
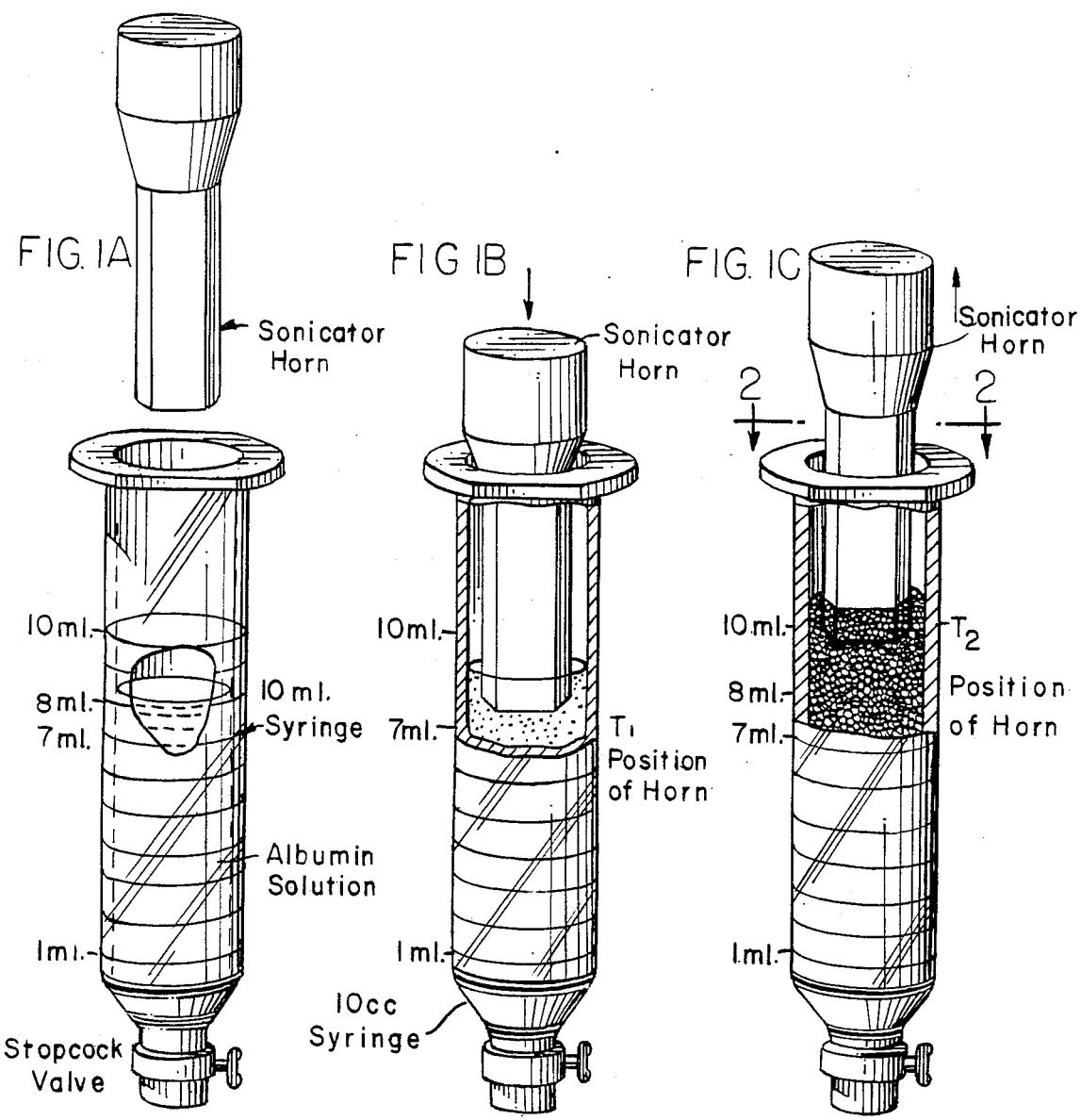
FIGS. 1A to 1D illustrate the steps in the sequential sonication procedure.

In FIG. 1A, there is shown a 10 ml syringe having an open top and a stopcock-type valve at its lower discharge end. The syringe is filled to the 8 ml level with the 5% albumin (HSA) solution. The sonicator horn is inserted in the syringe to the 7 ml level, indicated as the $T_1$ position in FIG. 1B. In this position, the sonicator horn is immersed in the upper portion of the solution, the solution level being as indicated in FIG. 1B. Initial sonication is carried out essentially without foaming of the solution.

Figure 1D:
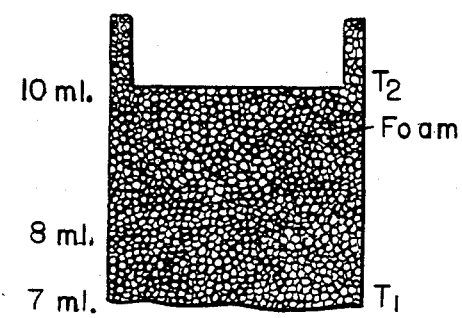

Immediately following initial sonication and without turning off the sonicator, the horn is withdrawn to the 10 ml level, indicated as the $T_2$ position in FIG. 1C. The power input to the sonicator horn can also be increased as it is withdrawn to the $T_2$ position. Immediately following the withdrawal, foaming of the albumin solution commences and the solution becomes milky in appearance. The solution will foam upwardly around the sonicator horn during the second phase. The appearance of the foamed solution is illustrated in FIG. 1D, the microbubbles being indicated in greatly enlarged diameter over their actual micron range sizes.

Figure 2:
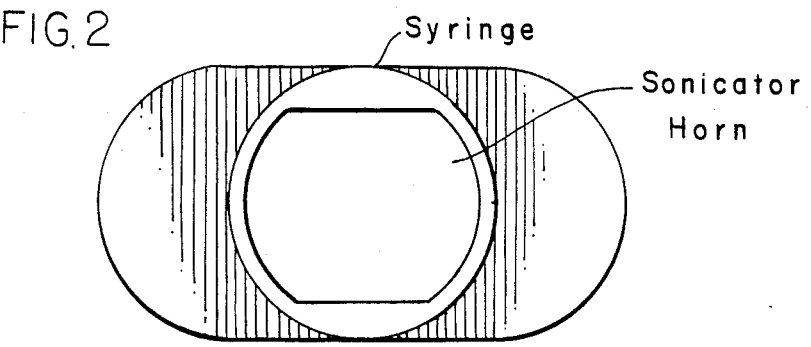
FIG. 2 is a cross-sectional view taken on line 2—2 of FIG. 1B, illustrating the relation of the sonicator horn to the inside of the syringe which contains the albumin solution being sonicated.

The solution being sonicated contains both dissolved and entrained air. The solution is in contact with the ambient atmosphere around the sonicator horn. (The clearance between the horn and the inside of the syringe can be seen in the cross-sectional view of FIG. 2.) The air contact facilitates the foaming and aerosolating of the solution in the second stage of the sonication.

Figure 3:
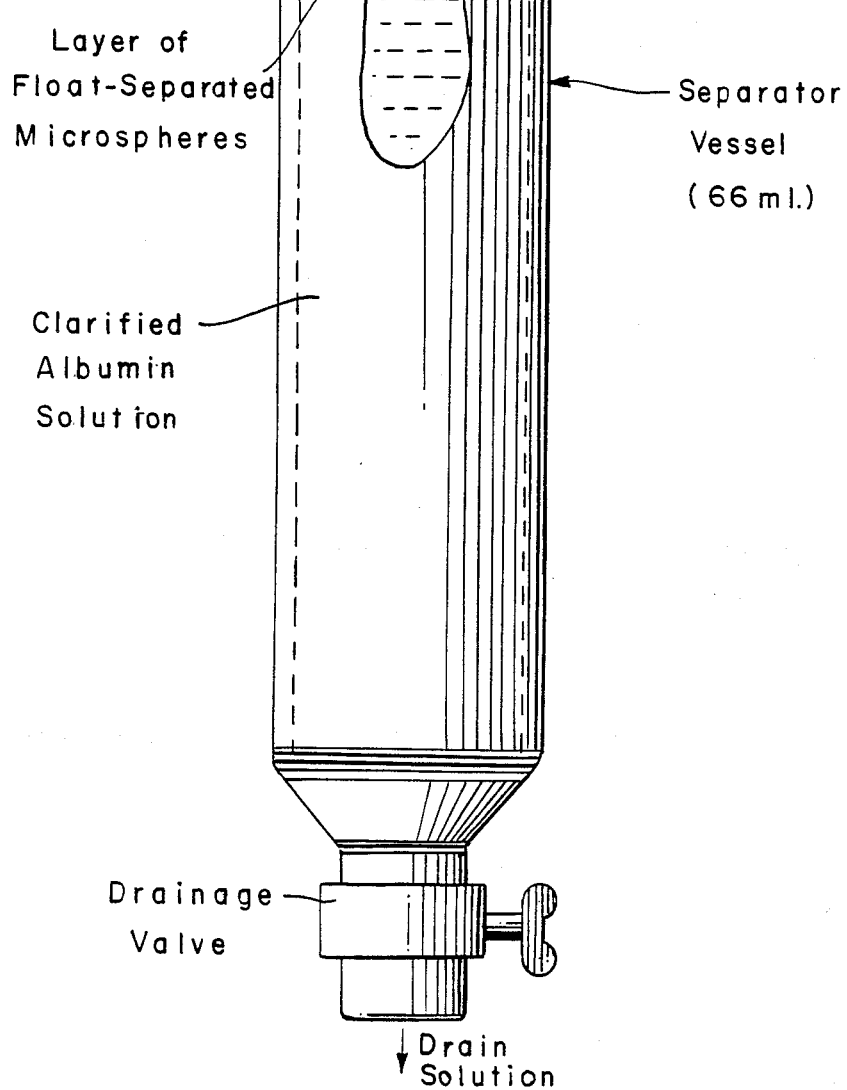
FIG. 3 illustrates a separator vessel in which increments of the microsphere dispersions are pooled for float separation concentration.

The dispersions from a plurality of sonication batches can be pooled for concentration. For example, a plurality of the dispersion increments can be introduced into a separator vessel, which may be a large syringe or separator funnel equipped at its bottom with an outlet controlled by a drainage valve. Such a separate vessel in the form of a large syringe is shown in FIG. 3. By holding the pooled dispersions for several hours without agitation, such as overnight holding, the microspheres will rise to the top of the solution and form a layer of float-separated microspheres. Beneath the collected layer, the clarified albumin solution will be substantially free of microspheres. It is therefore possible to drain off a major portion of the solution through the bottom outlet. For example, one-half to three-fourths of the solution can be removed. However, it is desirable to retain a sufficient solution volume to permit full redispersion of the concentrated microspheres.

In FIG. 4 illustrates the microsphere concentrate with the microspheres redispersed. The microspheres are sufficiently stable that they do not adhere permanently to each other in a concentrated layer, remaining as separate intact microspheres. They can readily be redispersed by mild agitation.

After redispersion to an essentially homogeneous condition, fractionation may be carried out to remove oversize microspheres. By holding the redispersion for a short time, such as around 30 minutes, the largest diameter microspheres will preferentially rise to the top and collect in a layer, as indicated in FIG. 4A. When that has occurred, the microsphere dispersion beneath the oversize microspheres can be removed through the drainage valve. When the collected oversize microspheres approach the valve, the valve is closed so that the oversize layer remains in the separator vessel, as indicated in FIG. 4B. The product obtained is a concentrated fractionated albumin microsphere product in which at least 80% of the microspheres have diameters in the range from 1 to 9 microns. The preferred product has at least 90% of the microspheres with diameters of from 2 to 8 microns.

Further directional details of the presently preferred procedures are set out below under the appropriate headings.

Sonication:

Fill a 10 ml syringe of oval cross-section fitted at its lower outlet end with a stopcock to the 8 ml mark with sterile 5% human serum albumin. Position a sonicator probe of smaller cross-section in the syringe so that the bottom of the probe is at the 7 ml mark. Sonicate at energy setting 6 for 30 seconds then (with the sonicator still on) move the probe tip to the 10 ml mark, while moving the energy setting to 8. Sonicate for an additional 25 seconds. Turn off sonicator, remove probe and drain contents of the syringe into a 60 ml syringe or separatory funnel with a stopcock controlled bottom outlet. From 5 to 6 syringe volumes are pooled.

Concentration:

Allow the pooled increments to stand overnight (8-12 hours) without agitation in the separator vessel. When substantially all the microspheres have formed a layer on the top, drain two-thirds of the volume from the bottom.

Fractionation:

Resuspend the microspheres and fill a 60 ml syringe with them. Let sit 30 minutes, then drain all but about the last 3-4 ml into a collection vessel. The oversize microspheres are left. Count a sample and calculate the concentration, mean diameter, and percentage less than 10 μ. If less than 99.5% are less than 10μ, re-fractionate. If required for redispersion, concentration may be adjusted with 5% HSA.

RESULTS

Concentration measurements are set out below in Table A for three representative runs using the procedures described above. The initial concentration of the disperions after sonication was of the order of 130 to $140 \times 10^6$/ml. This was increased by the float-separation concentration to 340 to $450 \times 10^6$/ml.

For product control, the microspheres may be counted by a Coulter Counter, obtainable from Coulter Electronics, Inc., Highleah, Fla. (viz. Coulter Counter Model TAII). Microsphere counts set out above were determined in this way.

The stability of a representative product was examined in a study lasting for 20 weeks. The initial concentration was approximately $4.31 \times 10^8$ ($431 \times 10^6$) microspheres per milliliter. Concentration measurements were made at about weekly intervals. The results are summarized in Table B. The measurements, which were made by means of a Coulter Counter, are presented graphically in FIG. 5. The samples were held at ambient room temperature (20°-25° C.). The concentration of about $400 \times 10^6$ microspheres per milliliter was maintained for 20 weeks. This evidences a high degree of room temperature stability.

The stability of the microspheres can be affected by unusually hot or cold temperatures. However, even at temperatures as low as 4° C. or as high as 37° C., microsphere concentrations in excess of $200 \times 10^6$/ml can be maintained for periods of eight weeks or longer. Nevertheless, for commercial distribution or long-term holding very high or low temperatures should be avoided. Room temperature holding is preferred. Temperature protection of the microspheres during shipment can be used.

TABLE A

Concentration Measurements

| Runs | Microspheres/ml After Sonication | Microspheres/ml After Concentration |
|---|---|---|
| A | $135 \times 10^6$ | $386 \times 10^6$ |
| B | $141 \times 10^6$ | $483 \times 10^6$ |
| C | $133 \times 10^6$ | $440 \times 10^6$ |

TABLE B

| Week | Microsphere Concentration $\times 10^8$ |
|---|---|
| 0 | 4.31 |
| 1 | 4.49 |
| 2 | 4.20 |
| 3 | 3.91 |
| 4 | 3.86 |
| 5 | 4.25 |
| 6 | 4.06 |
| 7 | 4.12 |
| 8 | 3.92 |
| 9 | 3.94 |
| 10 | 3.97 |
| 11 | 3.48 |
| 12 | 3.48 |
| 13 | 4.09 |
| 14 | 3.70 |
| 15 | 4.92 |
| 17 | 4.15 |
| 18 | 3.99 |
| 19 | 4.14 |

REFERENCES

Feigenbaum, et al. (1970), *Circulation* 41:615-621
Feinstein U.S. Pat. No. 4,572,203.
Feinstein PCT Application WO No. 84/02838.
Feinstein, et al. (1984), *J. Am. Coll. Cardiol.* 3:14-20.
Gramiak and S
Tickner et al. U.S. Pat. No. 4,276,885.
Tickner et al., National Technical Information Service Report HR 62917-1A, April, 1977, pages 34-40.

We claim:

1. A concentrated, storable ultrasonic imaging agent, comprising an aqueous parenteral medium containing a dispersion of microspheres predominantly of diameters less than 10 microns, said microspheres consisting of gas microbubbles enclosed by solid walls formed from heat-insolubilized biocompatible material, said imaging agent having a homogeneously dispersed concentration of greater than $1 \times 10^8$ microspheres per milliliter, said microspheres being stable in said medium as evidenced by maintaining a concentration of greater than $1 \times 10^8$ microspheres per milliliter for over 4 weeks at a temperature of 20° to 25° C.

2. The imaging agent of claim 1 in which said biocompatible material is a heat sensitive protein.

3. The imaging agent of claims 1 or 2 in which at least 80% of said microspheres have diameters in the range from 1 to 9 microns.

4. The imaging agent of claim 1 in which said biocompatible material is human serum albumin.

5. The imaging agent of claims 1 or 4 in which said gas is air.

6. A concentrated, storable ultrasonic imaging agent comprising an aqueous parenteral medium containing a dispersion of microspheres at least 80% of which have diameters in the range of 1 to 9 microns, said microspheres consisting of gas microbubbles enclosed by solid walls formed from heat-insolubilized protein, said imaging agent having a homogeneously dispersed concentration of greater than $1 \times 10^8$ microspheres per milliliter, said microspheres being stabilized in said medium as evidenced by maintaining a concentration of greater than $1 \times 10^8$ microspheres per milliliter for over 4 weeks at a temperature of 20° to 25° C.

7. The imaging agent of claim 6 in which said protein is human serum albumin and said gas is air.

8. The imaging agent of claims 6 or 7 in which said medium is an aqueous solution of the protein of the microsphere walls.

* * * * *

UNITED STATES PATENT AND TRADEMARK OFFICE

CERTIFICATE EXTENDING PATENT TERM
UNDER 35 U.S.C. § 156

PATENT NO.      :   4,844,882

ISSUED          :   July 4, 1989

INVENTOR(S)     :   Kenneth J. Widder

PATENT OWNER    :   Molecular Biosystems, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 220 days from the date of expiration of the original patent term, December 29, 2007, with all rights pertaining thereto as provided by 35 U.S.C. § 156(b).

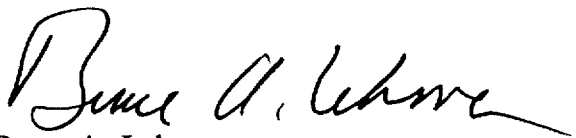

I have caused the seal of the Patent and Trademark Office to be affixed this 23rd day of September 1996.

Bruce A. Lehman
Assistant Secretary of Commerce and
Commissioner of Patents and Trademarks